(12) United States Patent
Shipley (10) Patent No.: US 9,974,627 B2
(45) Date of Patent: May 22, 2018

(54) METHOD FOR CUTTING OR ABRADING WITH A TOOL, AND RELATED DRIVERS AND SYSTEMS

(71) Applicant: Aseptico Inc., Woodinville, WA (US)

(72) Inventor: James Shipley, Monroe, WA (US)

(73) Assignee: Aseptico Inc., Woodinville, WA (US)

( * ) Notice: Subject to any disclaimer, the term of this patent is extended or adjusted under 35 U.S.C. 154(b) by 558 days.

(21) Appl. No.: 14/390,361

(22) PCT Filed: Apr. 8, 2013

(86) PCT No.: PCT/US2013/035606
§ 371 (c)(1),
(2) Date: Oct. 2, 2014

(87) PCT Pub. No.: WO2013/152346
PCT Pub. Date: Oct. 10, 2013

(65) Prior Publication Data
US 2015/0125807 A1    May 7, 2015

Related U.S. Application Data

(60) Provisional application No. 61/621,180, filed on Apr. 6, 2012.

(51) Int. Cl.
*A61C 1/00* (2006.01)
*A61C 3/00* (2006.01)
(Continued)

(52) U.S. Cl.
CPC ........ *A61C 1/0015* (2013.01); *A61B 17/1626* (2013.01); *A61C 1/003* (2013.01);
(Continued)

(58) Field of Classification Search
CPC .......... A61C 1/00–1/0038; A61C 1/18–1/188; A61C 3/00; A61C 3/02; A61C 5/02; A61C 17/1626; A61C 17/32002
(Continued)

(56) References Cited

U.S. PATENT DOCUMENTS 3,852,884 A * 12/1974 Lazarus .................... A61C 3/00
433/141
4,142,138 A * 2/1979 Taylor ...................... B04B 9/02
318/541

(Continued)

FOREIGN PATENT DOCUMENTS

| DE | 102010027631 A1 | 1/2012 |
|---|---|---|
| JP | H0938108 A | 2/1997 |
| WO | 2010066337 A1 | 6/2010 |

*Primary Examiner* — Loan H Thanh
*Assistant Examiner* — Garrett Atkinson
(74) *Attorney, Agent, or Firm* — Janeway Patent Law PLLC (57) ABSTRACT

A method for cutting with a tool comprises rotating the tool in a first direction. Then, at a predetermined moment, quit rotating the tool and allow the tool to coast in the first direction. While the tool coasts, a parameter is determined that represents drag experienced by the tool as the tool coasts. If the determined parameter does not exceed a predetermined limit then the tool is rotated in the first direction. If the determined parameter exceeds the predetermined limit, then the tool is rotated in another direction opposite the first direction. The predetermined moment when the tool begins to coast may be any desired moment, such as when the tool rotates through a specific distance or for a specific period of time.

19 Claims, 4 Drawing Sheets

(51) Int. Cl.
*A61B 17/16* (2006.01)
*A61C 1/18* (2006.01)
*A61C 3/02* (2006.01)
*A61C 5/40* (2017.01)
*A61B 17/32* (2006.01)
*A61B 17/00* (2006.01)

(52) U.S. Cl.
CPC ........... *A61C 1/186* (2013.01); *A61C 3/02* (2013.01); *A61C 5/40* (2017.02); *A61B 17/32002* (2013.01); *A61B 2017/00075* (2013.01)

(58) Field of Classification Search
USPC ....... 433/25, 27–28, 103, 114, 118–133, 224
See application file for complete search history.

(56) References Cited

U.S. PATENT DOCUMENTS

| | | | | |
|---|---|---|---|---|
| 4,412,158 A | * | 10/1983 | Jefferson | H02P 25/145 318/257 |
| 4,436,091 A | | 3/1984 | Banko | |
| 4,551,097 A | * | 11/1985 | Lazarus | A61C 5/85 433/39 |
| 4,857,814 A | * | 8/1989 | Duncan | D06F 37/306 318/281 |
| 5,568,026 A | * | 10/1996 | Welch | B60S 1/0814 318/41 |
| 5,980,248 A | * | 11/1999 | Kusakabe | A61C 1/0007 433/131 |
| 6,293,795 B1 | | 9/2001 | Johnson | |
| 6,350,125 B1 | * | 2/2002 | Matsutani | A61C 1/12 433/118 |
| 6,616,446 B1 | * | 9/2003 | Schmid | A61B 17/14 433/131 |
| 6,929,476 B2 | * | 8/2005 | Katsuda | A61C 1/0015 433/118 |
| 9,041,323 B2 | * | 5/2015 | Brown | A61C 1/003 318/267 |
| D767,766 S | * | 9/2016 | Sanga | D24/177 |
| 2011/0230868 A1 | | 9/2011 | Isobe et al. | |
| 2013/0234627 A1 | * | 9/2013 | Brown | A61C 1/003 318/3 |

\* cited by examiner

METHOD FOR CUTTING OR ABRADING WITH A TOOL, AND RELATED DRIVERS AND SYSTEMS

CROSS REFERENCE TO RELATED APPLICATION AND CLAIM OF PRIORITY

This application claims priority from commonly owned U.S. Provisional Patent Applications 61/621,180 filed 6 Apr. 2012, and titled "DUAL MODE INSTRUMENT DRIVER", which is incorporated by reference.

BACKGROUND

Dental and medical practitioners routinely perform dental/medical procedures that typically involve using a tool such as a file, bur, cutter, reamer, or polisher powered by a motor system to cut a patient's tooth, bone, or soft tissue. For example, when a patient has a decaying and/or infected tooth, a dentist or other medical technician will often use a file or reamer to remove the dental pulp from the patient's tooth and preserve the health of the patient's tooth and/or jaw. And, when a patient has a chipped tooth or a cavity, a dentist or other medical technician will often use a bur to remove some of the tooth's enamel to prevent further, additional damage to the tooth. To remove the dental pulp from a tooth the dentist or other medical technician inserts a file or reamer into the tooth's root canal. To remove enamel from a tooth the dentist or other medical technician places a burr or other type of tool on the region of the tooth's enamel to be removed. The motor of the motor system then rotates the tool to cut and/or abrade tissue and/or enamel from the patient's tooth.

There are two general types of rotary motion that the tool performs during such procedures—single-direction rotation and reciprocating rotation. During single-direction rotation, the tool rotates primarily in one direction, clockwise or counterclockwise. To avoid unwanted damage to the patient and the tool, the torque experienced by the tool as it rotates is monitored. If the torque exceeds a desired limit, then the tool is rotated in the opposite direction for a brief moment to unbind it. Then the tool's rotation is again reversed so that it resumes rotation in the direction in which it cuts and/or abrades. During reciprocating rotation, the tool rotates in two, opposite directions, sequentially. The trigger for reversing rotational direction is often a predetermined angular displacement or the end of a predetermined period of time.

Using single-direction rotation often provides good cutting efficiency because the tool rotates for longer periods of time in the direction that the tool is designed to cut and/or abrade. Using the reciprocating rotation often provides a dentist or other medical technician a good feel for the procedure because the motor does not continuously power or load the tool in a substantially-single direction.

Thus there is a need for a system that provides the two general types of rotary motion and can provide either type of rotary motion in response to the conditions experienced during the a procedure.

SUMMARY

In an aspect of the invention, a method for cutting with a tool comprises rotating the tool in a first direction. Then, at a predetermined moment, quit rotating the tool and allow the tool to coast in the first direction. While the tool coasts, a parameter is determined that represents drag experienced by the tool as the tool coasts. If the determined parameter does not exceed a predetermined limit then the tool is rotated in the first direction. If the determined parameter exceeds the predetermined limit, then the tool is rotated in another direction opposite the first direction. The predetermined moment when the tool begins to coast may be any desired moment, such as when the tool rotates through a specific distance or for a specific period of time.

By allowing the tool to coast, stress accumulated in the tool by the load imposed on the tool to rotate it may be relieved, and a dentist and/or medical technician can obtain a good feel for the procedure. That is, the dentist and/or medical technician can obtain a better sense of what the tool experiences as the tool rotates. And, by evaluating a parameter that represents the drag that the tool experiences as the tool coasts, one can accurately determine whether or not the tool should rotate reciprocally to help relieve stress in the tool and prevent unwanted damage to the patient and/or tool. If so, then the tool is rotated reciprocally until the conditions of the procedure suggest that the tool should be rotated in a single direction.

DETAILED DESCRIPTION

Figure 1:
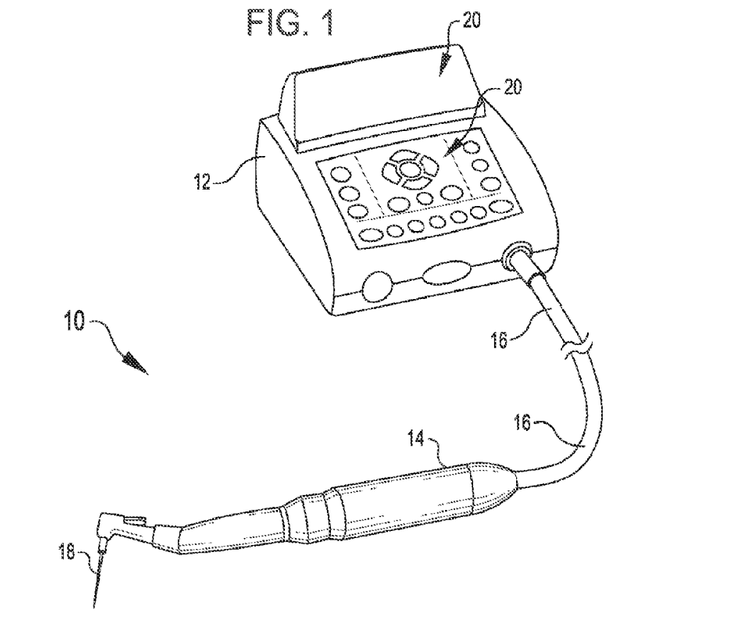
FIG. 1 is a perspective view of an endodontic system, according to an embodiment of the invention.

FIG. 1 is a perspective view of an endodontic system 10, according to an embodiment of the invention. The endodontic system 10 includes a body 12 housing control circuitry (not shown), a hand-piece 14 releasably coupled to the body 12 via a cable 16, and a tool 18 releasably coupled to the hand-piece 14. In this and other embodiments of the endodontic system 10, the hand-piece 14 includes a motor (not shown) that is coupled to the control circuitry inside the body 12 via the cable 16, and coupled to the tool 18 via a mechanical transmission (also not shown). In operation, the motor receives power (here electrical) from the control circuitry via the cable 16 and, in response, rotates the tool 18.

Based on the output that the tool 18 is designed to provide and/or the output that the motor is designed to provide, and based on actual feedback during operation, the control circuitry directs to output of the motor and/or the tool 18. To allow one to use a different hand-piece and tool 18 combination to perform a similar or a different procedure, the endodontic system 10 also includes a user interface 20 coupled to the control circuitry. With the user interface, one can select a specific operational protocol for the control circuitry to follow during a procedure, or one can modify, as desired, one or more operational parameters of a specific protocol for the endodontic system 10 to perform. One of the operational protocols available to the control circuitry of the system 10 includes a protocol (discussed in greater detail in conjunction with FIG. 2) that drives the tool 18 to rotate in a single direction unless the tool 18 experiences excessive torque upon which the tool 18 is rotated in the opposite direction for a short period to unbind the tool 18. Another of the operational protocols available to the control circuitry of the system 10 includes a protocol (discussed in greater detail in conjunction with FIGS. 3, 4 and 5) that drives the tool 18 to rotate for a period, then allows the tool 18 to coast for another period, and then depending on what happens during the coast period drives the tool 18 in the original direction or in an opposite direct.

By driving the tool 18 in a single direction unless the tool 18 experiences excessive torque allows one to efficiently cut or abrade tissue without damaging the tool or the patient should the tool experience a torque that could break the tool. By allowing the tool to coast, stress accumulated in the tool by the load imposed on the tool to rotate it may be relieved, and a dentist and/or medical technician can obtain a good feel for what the tool 18 experiences during the procedure. And, by evaluating what the tool 18 experiences as the tool 18 coasts, one can accurately determine whether or not the tool 18 should rotate reciprocally to relieve stress in the tool and to help prevent unwanted damage to the patient and/or tool. If so, then the tool is rotated reciprocally until the conditions of the procedure suggest that the tool should be rotated in a single direction.

Still referring to FIG. 1, in this and other embodiments of the system 10, one manually instructs the control circuitry to follow either of the two protocols. To decide which protocol to use, one considers the procedure to be performed, the specific tool to be used, and information related to the specific patient. If the procedure is routine and involves removing a minor amount of dental pulp for a patient's tooth, then one may prefer to use a file that is designed to cut when rotated in a single direction. In these circumstances, one may choose to have the control circuitry of the endodontic system 10 follow the protocol that drives the tool 18 to rotate in a single direction unless the tool 18 experiences excessive torque upon which the tool 18 is rotated in the opposite direction for a short period to unbind the tool 18. If the procedure is not routine and involves removing dental pulp close to the tooth's apical foramen, then one may prefer to have a better feel of the action during the procedure. In these circumstances one may choose to have the control circuitry of the endodontic system 10 follow the protocol that drives the tool 18 to rotate for a period, then allows the tool 18 to coast for another period, and then depending on what happens during the coast period drives the tool 18 in the original direction or in an opposite direct.

Other embodiments are possible. For example the endodontic system 10 may automatically determine which of these operational protocols the control circuitry will follow. The system 10 may make this decision based on any desired operational parameter input by the user, such as a specific type of tool or a specific type of procedure.

Figure 2:
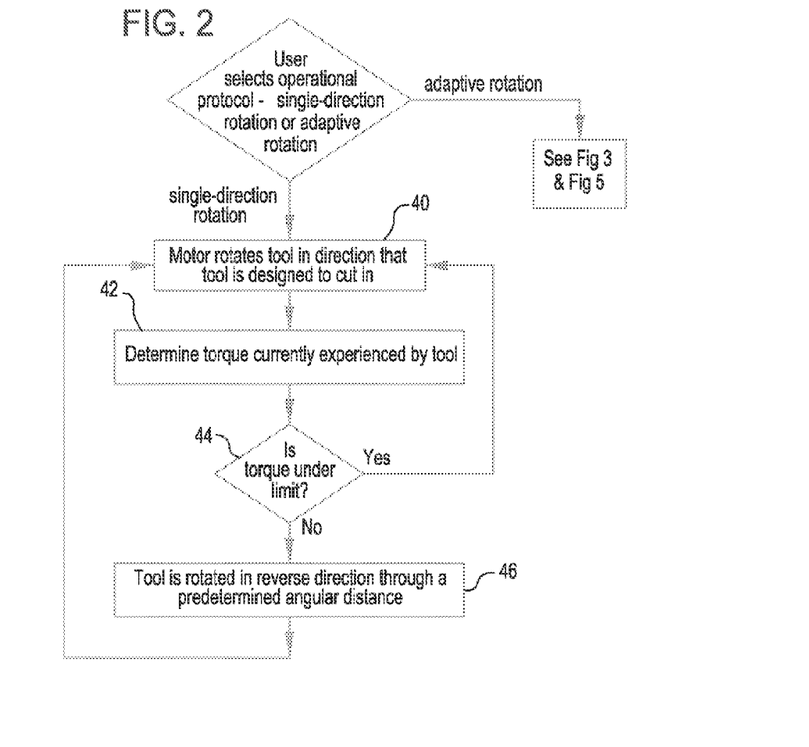
FIG. 2 is a schematic view of a method for cutting and/or abrading that the endodontic system of FIG. 1 may implement, according to an embodiment of the invention.

FIG. 2 is a schematic view of a method for cutting and/or abrading that the endodontic system of FIG. 1 may implement, according to an embodiment of the invention. The method includes the protocol that drives the tool 18 to rotate in a single direction unless the tool 18 experiences excessive torque, upon which the tool 18 is rotated in the opposite direction for a short period to unbind the tool 18. This protocol is identified as single-direction rotation because when the tool does not experience excessive torque, the control circuitry continuously drives the tool 18 in a single direction.

After one selects this protocol as discussed above, the first event 40 of the protocol is the motor rotates the tool 18 (FIG. 1) in the direction that the tool 18 is designed to cut in. To do this the control circuitry sends power and a control signal to the motor in the hand-piece 14 (FIG. 1) via the cable 16 (FIG. 1). In response, the motor rotates the tool 18 via the transmission disposed in the hand-piece 14. The amount of power and the direction of rotation may be any desired amount and direction that allows the motor to rotate the tool 18 as desired. For example, the tool 18 selected for the procedure may best perform rotating clockwise at 300 to 500 rpms while experiencing 100 to 500 gram-centimeters (gcm) of torque. To provide these operational parameters to the tool 18, the control circuitry matches the specific motor and transmission combination with the amount of electrical power needed by the motor. In this embodiment of the system 10 (FIG. 1), the control circuitry automatically detects the specific motor and transmission combination and determines how much electrical power the motor requires to provide a specific set of operational parameters. In other embodiments, one may input the desired motor and transmission combination and/or the desired operational parameters for the tool 18 via the user interface 20 (FIG. 1).

Then, in the next event 42, the control circuitry determines the torque currently experienced by the rotating tool 18. The current torque may be determined in any desired manner. For example, the control circuit may measure, at any desired moment, the amount of electrical power consumed by the motor and the tool's rotational speed. The tool's rotational speed decreases as the torque that it experiences increases. Thus, for a known amount of power consumption, the rotational speed of the tool 18 may be used to determine the amount of torque experienced by the tool 18.

Then, in the next event 44, the control circuitry compares the current torque with a predetermined torque value. If the current torque experienced by the tool 18 does not exceed the predetermined value, then the control circuitry continues providing the electrical power and control signal to the motor that, in response, continues to rotate the tool 18 as desired. If, however, the current torque experienced by the tool 18 exceeds the predetermined value, then in the next event 46 the control circuitry sends a control signal that causes the tool 18 to rotate in the opposite direction to attempt to unbind the tool 18. The control circuit may reverse the rotational direction of the tool 18 in any desired manner. For example, in this and other embodiments, the control circuit may send the motor a control signal that causes the motor to immediately stop and rotate in reverse. In other embodiments, the control circuit may send the transmission a control signal that causes the transmission to mechanically reverse the direction that the tool 18 rotates.

Figure 3:
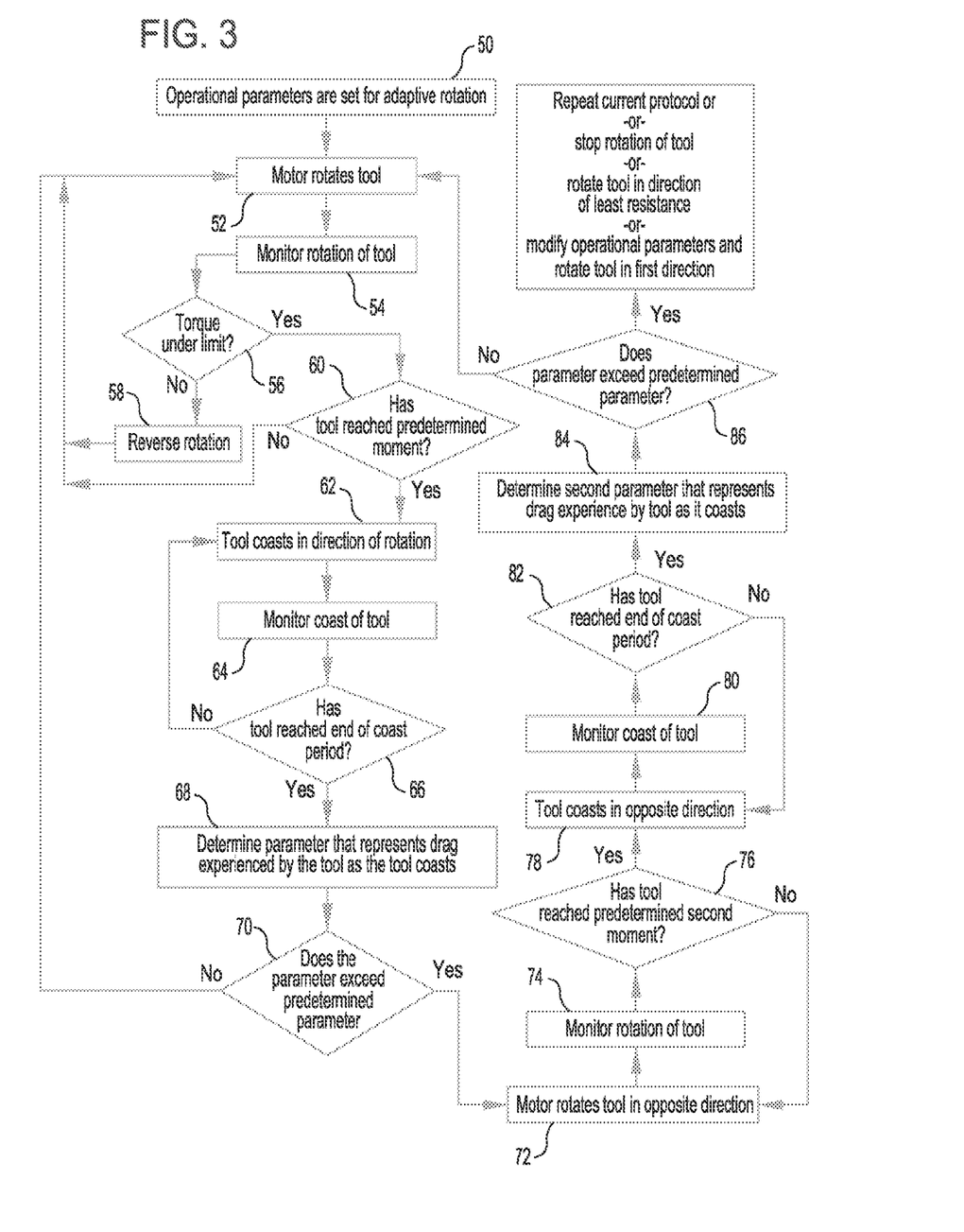
FIG. 3 is a schematic view of another method for cutting and/or abrading that the endodontic system of FIG. 1 may implement, according to an embodiment of the invention.

FIG. 3 is a schematic view of another method for cutting and/or abrading that the endodontic system of FIG. 1 may implement, according to an embodiment of the invention. The method includes the protocol that drives the tool 18 to rotate for a period, then allows the tool 18 to coast for another period, and then depending on what happens during the coast period drives the tool 18 to rotate in the original direction or in an opposite direct. By allowing the tool 18 to coast, one can obtain a good feel for what the tool 18 experiences during the procedure. And, by evaluating what the tool 18 experiences as the tool 18 coasts, one can more accurately determine whether or not the tool 18 should rotate reciprocally to help prevent unwanted damage to the patient and/or tool. If so, then the tool is rotated reciprocally until the conditions of the procedure suggest that the tool should be rotated in a single direction. This protocol is identified as adaptive rotation because the control circuitry modifies the rotation of the tool 18 based on what the tool experiences while coasting.

Referring to FIG. 3, after one selects this protocol as discussed above, the first event 50 of the protocol is to set the desired values (discussed in greater detail in the following paragraphs) for the protocol's operational parameters. These values may be set manually by the dentist and/or medical technician, or automatically by the control circuitry.

The next event 52 of the protocol is the motor rotates the tool 18 (FIG. 1) in a first direction. With the adaptive-rotation protocol, one may use a tool 18 that is designed to cut and/or abrade when it rotates in both the clockwise and the counterclockwise directions. Thus, the first direction that the tool 18 may rotate may be clockwise or counterclockwise, as desired. Once the first direction is established, the control circuitry sends power and a control signal to the motor in the hand-piece 14 (FIG. 1) via the cable 16 (FIG. 1). In response, the motor rotates the tool 18 via the transmission disposed in the hand-piece 14. Similar to the single-direction protocol discussed in conjunction with FIG. 2, the amount of power may be any desired amount that allows the motor to rotate the tool 18 as desired.

Still referring to FIG. 3, in the next event 54, the control circuitry monitors the rotation of the tool 18 in the first direction during the drive period to determine whether or not the tool experiences an excessive torque, and if the tool 18 doesn't, then to determine when the drive period ends. The control circuitry may monitor this in any desired manner. For example, similar to event 42 discussed in conjunction with FIG. 2, the control circuitry may measure, at any desired moment in the drive period, the amount of electrical power consumed by the motor and the tool's rotational speed, and from these determine a torque currently experienced by the tool 18. To determine when the drive period ends, in this and other embodiments, the control circuitry may monitor the angular displacement of the tool 18. In other embodiments, the control circuitry may monitor a period of time that the tool 18 rotates in the first direction. In still other embodiments, the control circuitry may monitor the rotational speed of the tool 18. This may be desirable when one wants to accelerate the tool 18 while the tool cuts and/or abrades tissue. By monitoring the rotational speed of the tool in such a situation, one can help prevent the tool 18 from over revving. In yet other embodiments, the control circuitry may monitor two or more of the following: the angular displacement of the tool 18, the period of time that the tool 18 rotates, and the rotational speed of the tool 18.

In event 56 and similar to event 44 also discussed in conjunction with FIG. 2, the control circuitry compares the current torque with a predetermined torque value. If the current torque experienced by the tool 18 exceeds the predetermined value, then, in event 58 and similar to event 46 discussed in conjunction with FIG. 2, the control circuitry sends a control signal that causes the tool 18 to briefly rotate in the opposite direction to attempt to unbind the tool 18. After briefly rotating in the opposite direction, the control circuitry proceeds back to event 52 and begins the drive period again. If, however, the current torque experienced by the tool 18 does not exceed the predetermined value, then the control circuitry continues to instruct the motor to rotate the tool 18 in the first direction, and proceeds to event 60.

In event 60, the control circuitry determines whether or not the tool's rotation has reached a predetermined moment that establishes the beginning of the tool's coast period. The predetermined moment may be any desired moment. For example, if the control circuitry monitors angular displacement, then the predetermined moment may be 640 degrees. If the control circuitry monitors a period of time, then the predetermined moment may be 120 microseconds. And, if the control circuitry monitors the rotational speed of the tool 18, then the predetermined moment may be 900 rpms. If the rotation of the tool 18 has not reached the predetermined moment, then the control circuitry continues to instruct the motor to drive the tool 18 in the first direction. If the rotation of the tool 18 reaches the predetermined moment, then the control circuitry proceeds to the next event 62.

In event 62, the control circuitry sends a control signal that causes the motor to quit rotating the tool 18, and allow the tool 18 to coast in the first direction. Because the motor does not drive the tool 18 while the tool coasts, the tool 18 is allowed to relieve stress accumulated under the load imposed on it by the motor. This, in turn, allows the tool 18 to transmit to the dentist's and/or medical technician's hand vibrations that provide a more accurate feel for what the tool experiences during a procedure.

The duration of the coast period may be any desired duration. For example, in this and other embodiments the coast period may be defined by a specific angular displacement of the tool 18 during the coast period, such as 90 degrees. In other embodiments, the coast period may be defined by the passage of specific period of time such as 40 microseconds. In still other embodiments, the coast period may be defined by a specific difference in the tool's rotational speed, such as a total change of 500 rpms, or a specific final rpm of 100 or even 0.0.

As the tool 18 coasts during the coast period, the control circuitry determines a parameter that represents the drag experienced by the tool 18 as the tool 18 coasts. The parameter may be any desired parameter that allows the control circuitry to determine the drag at either a specific moment during the coast period, or an amount of drag experienced over the whole or a portion of the coast period. For example, in this and other embodiments, the parameter is the tool's rotational speed. In event 64 the control circuitry monitors the coast period, and in event 66 the control circuitry determines whether or not the coast period ends. In event 68, when the tool 18 reaches the end of the coast period, the control circuitry determines the rotational speed of the tool and determines the amount of torque experienced through the whole coast period by subtracting the rotational speed of the tool 18 at the end of the coast period from the rotational speed of the tool 18 at the beginning of the coast period.

Still referring to FIG. 3, in event 70, the control circuitry then determines in which direction the tool 18 should rotate next. If the amount of torque experienced by the tool 18 through the coast period does not exceed a predetermined value, then, the control circuitry proceeds back to event 52 and sends power and a control signal to the motor to rotate the tool 18 in the first direction. The control circuitry then proceeds through events 54-70, again. If, however, the amount of torque experienced by the tool 18 through the coast period exceeds a predetermined value, then the control circuitry proceeds to events 72-76, in which the control circuitry sends power and a control signal to the motor to rotate the tool 18 in a direction opposite the first direction.

Events 72-76 are similar to events 52-60, except that the control circuitry sends power and a control signal to the motor that causes the motor to rotate the tool 18 in a direction opposite the first direction. In addition, the duration of the reverse-drive period is often different than, but may be the same as, the duration of the drive period discussed in events 52-60. In this and other embodiments, the duration of the reverse-drive period is less than the duration of the drive period. Specifically, the drive period is determined by the tool's angular displace of 20 degrees. In addition, the tool's angular displacement is measured as an absolute value. That is, if the tool 18 rotates in the first direction for 5 degrees during a first portion of the reverse-drive period, and then rotates 15 degrees in the opposite direction, the reverse-drive period would end when the tool reached 15 degrees in the opposite direction.

Other embodiments are possible. For example, during the reverse-drive period the control circuitry may not test for and react to excessive torque experienced by the tool 18, as discussed in events 56 and 58.

After the reverse-drive period, the tool 18 experiences a reverse-coast period. During the reverse-coast period, the control circuitry determines a second parameter that represents drag experienced by the tool 18 during the reverse-coast period, and in response, determines how to proceed. In this and other embodiments, the options for proceeding include repeating the current protocol, and rotating the tool 18 in the direction that the tool experiences less torque, which may be different that the first direction, and may be according to a different protocol, such as the protocol discussed in conjunction with FIG. 2. The options for proceeding also include stopping the rotation of the tool 18, and modifying one or more of the operational parameters in the current protocol and rotating the tool 18 according to the modified protocol.

The reverse-coast period, events 78-82, is similar to the coast period discussed in conjunction with events 62-66, except that the tool's rotation is often, but not necessarily, opposite the rotation of the tool 18 during the coast period, events 62-66, and is often shorter in duration than the coast period, 62-66. Likewise, determining the second parameter that represents drag experienced by the tool 18 during the reverse-coast period, events 84 and 86, is similar to determining the first parameter that represents drag experienced by the tool 18 during the coast period, events 68 and 70, except that the values of the torque are often, but not necessarily, less than the torque values used and experienced during the coast period, events 68 and 70.

Figure 4:
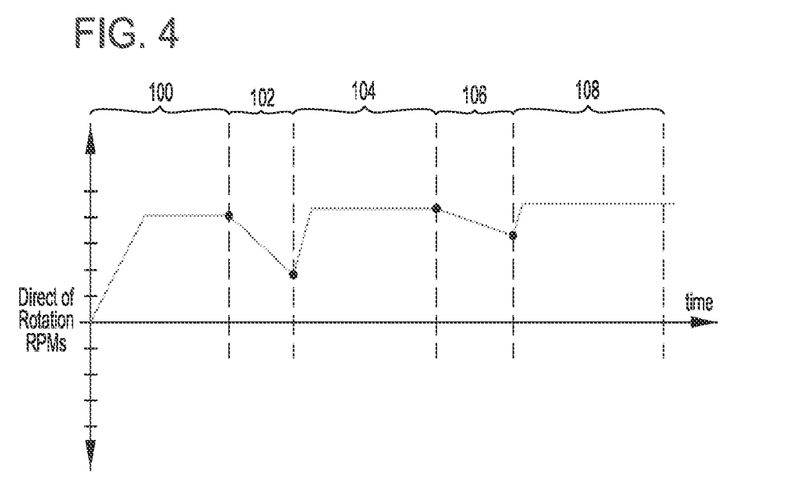
FIG. 4 is a graphic illustration of the method shown in FIG. 3, according to an embodiment of the invention.
Figure 5:
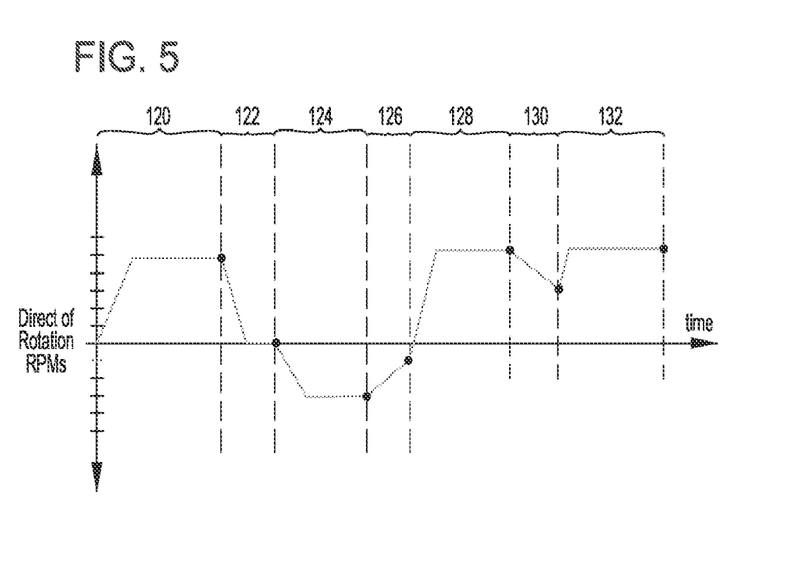
FIG. 5 is another graphic illustration of the method shown in FIG. 3, according to an embodiment of the invention.

FIGS. 4 and 5 are graphic illustrations of the adaptive-rotation protocol discussed in conjunction with FIG. 3, each according to an embodiment of the invention. The graph shown in FIG. 4 illustrates the protocol that drives the tool 18 to rotate in the first direction for a period, then allows the tool 18 to coast for another period, and then drives the tool 18 to again rotate in the first direction. This cycle can occur when the amount of torque experienced by the tool 18 through the coast period does not exceed the predetermined value. The graph shown in FIG. 5 illustrates the protocol that drives the tool 18 to rotate in the first direction for a period, then allows the tool 18 to coast for another period, then drives the tool 18 to rotate in a direction opposite the first direction, and then drives the tool 18 to again rotate in the first direction. This cycle can occur when the amount of torque experienced by the tool 18 through the coast period exceeds the predetermined value. Also illustrated in FIG. 5 is the change in protocol from one cycle of reverse-direction rotation to a subsequent cycle of drive-coast-drive periods each in the first direction.

Referring to FIG. 4, in this and other embodiments, the drive period 100 represents the drive period discussed in conjunction with events 52-60 in FIG. 3. The coast period 102 represents the coast period discussed in conjunction with events 62-70 in FIG. 3. The next drive period 104 is the beginning of the next cycle and represents the drive period discussed in conjunction with events 52-60 in FIG. 3. The next coast period 106 represents the coast period discussed in conjunction with events 62-70 in FIG. 3. And, the next drive period 108 is the beginning of the third cycle and represents the drive period discussed in conjunction with events 52-60 in FIG. 3.

Referring to FIG. 5, in this and other embodiments, the drive period 120 represents the drive period discussed in conjunction with events 52-60 in FIG. 3. The coast period 122 represents the coast period discussed in conjunction with events 62-70 in FIG. 3. The reverse-drive period 124 represents the reverse-drive period discussed in conjunction with events 72-76 in FIG. 3. The reverse-coast period 126 represents the reverse-coast period discussed in conjunction with events 78-86 in FIG. 3. The next drive period 128 is the beginning of the next cycle, which is different than the previous cycle, and represents the drive period discussed in conjunction with events 52-60 in FIG. 3. The next coast period 130 represents the coast period discussed in conjunction with events 62-70 in FIG. 3. And, the next drive period 132 is the beginning of next cycle and represents the drive period discussed in conjunction with events 52-60 in FIG. 3.

Figure 6:
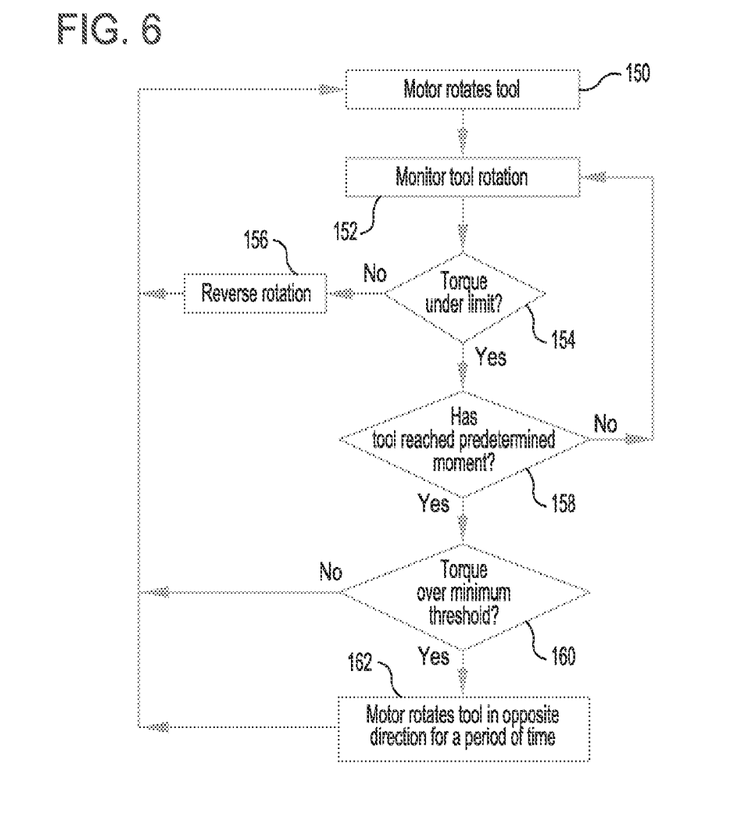
FIG. 6 is a schematic view of a method for cutting and/or abrading that the endodontic system of FIG. 1 may implement, according to another embodiment of the invention.

FIG. 6 is a schematic view of another method for cutting and/or abrading that the endodontic system of FIG. 1 may implement, according to an embodiment of the invention. This method includes a protocol that drives the tool 18 to rotate in a first direction for a period, and then at the end of the period determines whether to drive the tool 18 in the same direction for another period or drive the tool 18 in an opposite direction. If the tool 18 experiences a torque during the drive period that exceeds a minimum threshold value, then the tool 18 is rotated for a period in a direction opposite the first direction. If the tool 18 does not experience a torque during the drive period that exceeds a minimum threshold value, then the tool 18 is rotated in the first direction for another period of time. By reversing the rotation of the tool 18 after the tool 18 experiences a torque that exceeds a minimum value, the tool 18 is allowed to relieve stress accumulated under the load imposed on it by the motor during the drive period.

This protocol is similar to the protocol discussed in conjunction with FIG. 3, except that this protocol does not include a coast period after the first-direction drive period, or after a reverse-drive period. More specifically, events 150-158 are similar to events 52-60, respectively, and as such the discussion of the events 52-60 applies to events 150-158. A difference between this protocol and the protocol discussed in conjunction with FIG. 3 is that in event 160 the control circuitry compares the torque experienced by the tool 18 during the period that the motor drives the tool 18 in the first direction with a predetermined minimum threshold torque.

Referring to FIG. 6, the minimum threshold torque may be any desired minimum and may be manually input by a user for use by the control circuitry, or automatically input. In this and other embodiments, the minimum threshold torque is 50 gcm and the maximum predetermined torque limit used by the control circuitry to protect against breaking the tool 18 is 300 gcm. Thus, if the tool 18 does not experience a torque that exceeds 300 gcm, then the control circuitry will rotate the tool until the drive period ends. At the end of the drive period, the control circuitry then determines whether or not the tool 18 experienced a torque that exceeds the minimum threshold. If the tool 18 did not, then the control circuitry proceeds back to event 150 and instructs the motor to drive the tool 18 in the first direction for another period. If the tool 18, however, does experience a torque that exceeds the minimum threshold, for example 60 gcm, then the control circuitry proceeds to event 162 in which the control circuitry instructs the motor to rotate the tool 18 in reverse. Event 162 is similar to event 72 and 76 discussed in conjunction with FIG. 3, and as such, the discussion of the events 72 and 76 applies to event 162.

The control circuitry may determine the torque experienced by the tool 18 in any desired manner. For example, in this and other embodiments, the control circuitry may monitor the angular displacement of the tool 18 over a period. In other embodiments, the control circuitry may monitor a period of time that the tool 18 takes to rotate a specific angular distance. In still other embodiments, the control circuitry may monitor the rotational speed of the tool 18. In yet other embodiments, the control circuitry may monitor two or more of the following: the angular displacement of the tool 18, the period of time that the tool 18 rotates, and the rotational speed of the tool 18.

Other embodiments of the protocol are possible. For example, similar to the protocol discussed in conjunction with FIG. 3, the control circuitry may determine torque experienced by the tool 18 during the reverse-drive period, and in response, determine how to proceed. Options for proceeding may include repeating the current protocol, and rotating the tool 18 in the direction that the tool experiences less torque, which may be different that the first direction, and may be according to a different protocol, such as the protocol discussed in conjunction with FIG. 2 and/or FIG. 3. The options for proceeding may also include stopping the rotation of the tool 18, and modifying one or more of the operational parameters in the current protocol and rotating the tool 18 according to the modified protocol. For example, the duration of the reverse-drive period may increase proportionally with the torque measured in the drive period and/or in the reverse-drive period.

The preceding discussion is presented to enable a person skilled in the art to make and use the invention. Various modifications to the embodiments will be readily apparent to those skilled in the art, and the generic principles herein may be applied to other embodiments and applications without departing from the spirit and scope of the present invention. Thus, the present invention is not intended to be limited to the embodiments shown, but is to be accorded the widest scope consistent with the principles and features disclosed herein.

What is claimed is:

1. A method for cutting with a medical tool, the method comprising:
rotating the tool in a first direction;
quit rotating the tool at a predetermined moment;
allowing the tool to coast in the first direction;
determining a parameter that represents drag experienced by the tool as the tool coasts; and
in response to the determined parameter:
rotating the tool in the first direction, if the determined parameter does not exceed a predetermined limit, and
rotating the tool in another direction opposite the first direction, if the determined parameter does exceed the predetermined limit.

2. The method of claim 1 wherein the predetermined moment includes at least one of the following: an angular displacement, a duration of rotation, and a speed of rotation.

3. The method of claim 1 wherein the parameter that represents drag experienced by the tool includes at least one of the following: an angular displacement, a duration of rotation, and a speed of rotation.

4. The method of claim 1 wherein the predetermined limit includes at least one of the following: an angular displacement, a duration of rotation, and a speed of rotation.

5. The method of claim 1 wherein:
the first predetermined moment includes an angular displacement of 370 degrees,
the parameter that represents drag experienced by the tool includes an angular displacement over a 40-millisecond period, and
the predetermined limit includes an angular displacement of 65 degrees, wherein if the tool rotates more than 65 degrees over the 40-millisecond period, then the tool is rotated in the first direction.

6. The method of claim 1 wherein:
the first predetermined moment includes an angular displacement of 370 degrees,
the parameter that represents drag experienced by the tool includes a duration to rotate through 20 degrees, and
the predetermined limit includes a duration of 10 milliseconds, wherein if the tool rotates through more than 20 degrees during the 10-millisecond duration, then the tool is rotated in the first direction.

7. The method of claim 1 wherein allowing the tool to coast includes allowing the tool to freely coast.

8. The method of claim 1 wherein rotating the tool includes providing electric current to an electric motor coupled to the tool.

9. The method of claim 1 wherein quit rotating the tool includes preventing electric current from reaching an electric motor coupled to the tool.

10. The method of claim 1 further comprising repeating the method.

11. The method of claim 1 further comprising quit rotating the tool in the other direction opposite the first direction at a predetermined second moment.

12. The method of claim 11 wherein the predetermined second moment includes at least one of the following: an angular displacement, a duration of rotation, and a speed of rotation.

13. The method of claim 11 further comprising allowing the tool to coast in the other direction opposite the first direction.

14. The method of claim 13 further comprising determining a second parameter that represents drag experienced by the tool as the tool coasts in the other direction opposite the first direction.

15. The method of claim 14 wherein the second parameter that represents drag experienced by the tool includes at least one of the following: an angular displacement, a duration of rotation, and a speed of rotation.

16. The method of claim 14 further comprising, in response to the determined second parameter:
rotating the tool in the first direction, if the determined parameter does not exceed a second predetermined limit,
rotating the tool in the direction in which the tool experiences the least drag, if the second determined parameter exceeds the predetermined limit.

17. The method of claim 14 further comprising, in response to the determined second parameter:
rotating the tool in the first direction, if the determined parameter does not exceed a second predetermined limit,
quit rotating the tool, if the second determined parameter exceeds the predetermined limit.

18. An endodontic system comprising:
a handpiece that includes a head operable to releasably hold a tool, and a motor operable to rotate the tool while the head holds the tool; and
control circuitry operable to:
- instruct the motor to urge the tool to rotate in a first direction,
- instruct the motor to quit urging the tool to rotate at a predetermined moment to allow the tool to coast in the first direction,
- determine a parameter that represents drag experienced by the tool as the tool coasts,
- if the determined parameter does not exceed a predetermined limit, then instruct the motor to urge the tool to rotate in the first direction, and
- if the determined parameter does exceed the predetermined limit, then instruct the motor to urge the tool to rotate in another direction opposite the first direction.

19. The system of claim 18 wherein the tool includes at least one of the following: a file and a burr.

* * * * *